United States Patent [19]

Martin et al.

[11] 4,338,928

[45] Jul. 13, 1982

[54] LIP SHIELD AND TREATMENT DEVICE

[76] Inventors: Leonard G. Martin, 301 Golden Isle Dr., Apt. 105, Hallandale, Fla. 33009; Herbert S. Leb, 671 NE. 195 St., Apt. 121, North Miami Beach, Fla. 33179

[21] Appl. No.: 185,103

[22] Filed: Sep. 5, 1980

[51] Int. Cl.³ .............................................. A61F 5/56
[52] U.S. Cl. ................................................... 128/136
[58] Field of Search .................. 128/136, 132 R, 260; 2/174, 2, 9

[56] References Cited

U.S. PATENT DOCUMENTS

| | | | |
|---|---|---|---|
| 648,028 | 4/1900 | Hooper | 128/136 |
| 1,943,751 | 1/1934 | Van Dunker . | |
| 1,949,013 | 2/1934 | Gilchrist . | |
| 2,023,900 | 12/1935 | Rally . | |
| 2,079,099 | 5/1937 | Barnett . | |
| 2,088,076 | 7/1937 | Winslow . | |
| 2,434,078 | 1/1948 | Malerman . | |
| 2,535,084 | 12/1950 | Meunier . | |
| 2,589,504 | 3/1952 | Miller | 128/136 |
| 2,640,991 | 6/1953 | Ernst . | |
| 3,096,761 | 7/1963 | Moffett | 128/136 |
| 3,126,550 | 3/1964 | Price . | |
| 3,527,219 | 9/1970 | Greenberg | 128/136 X |
| 4,040,127 | 8/1977 | Slovitt et al. . | |

Primary Examiner—John D. Yasko
Attorney, Agent, or Firm—Herman J. Hohauser

[57] ABSTRACT

A lip shade and treatment device comprising a one-piece member having the general configuration of the outer surface of a lip and a cross-section in the shape of a "U" to be worn on either the upper or lower lip of the user and having a lining on the interior surface upon which medication can be applied.

10 Claims, 5 Drawing Figures

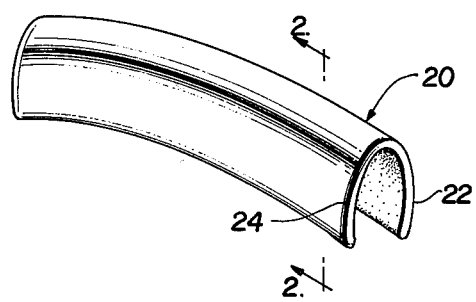
FIG.1
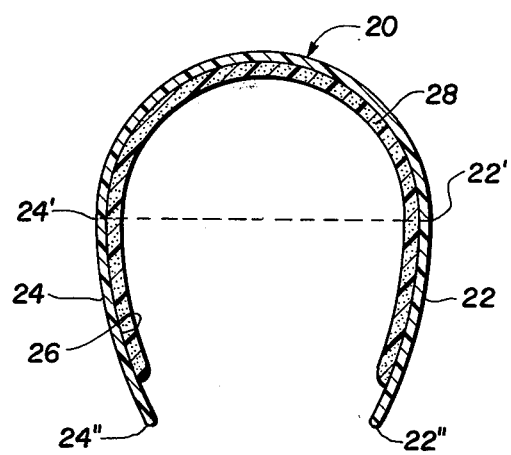
FIG.2
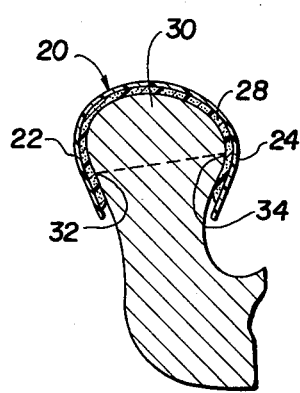
FIG.3
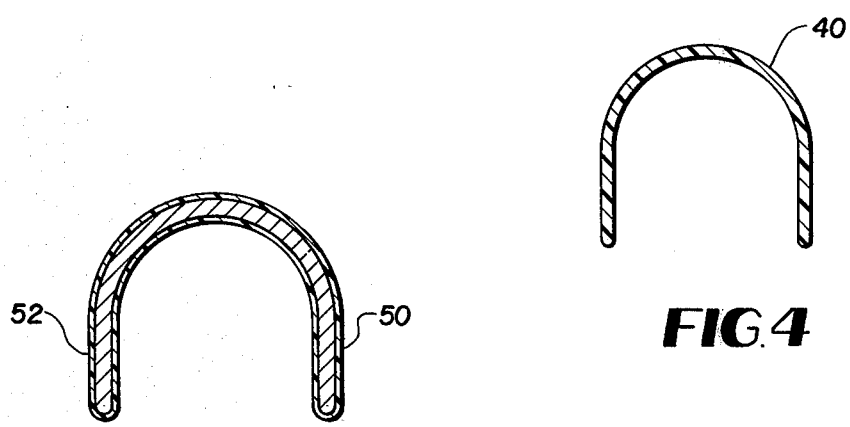
FIG.5          FIG.4

LIP SHIELD AND TREATMENT DEVICE

BACKGROUND OF THE INVENTION

The present invention relates generally to the field of preventive medicine and therapeutic devices and more particularly to a new device to aid in the prevention and/or therapy of pathologies of the lips.

It is well known that the two fleshy folds that surround the mouth in humans referred to as "lips" are extremely sensitive parts of the human body. The lips are constantly subjected to potentially harmful exposure from elements of the environment including radiation as from the sun, extreme weather conditions, wind, air pollutants and the like and are further susceptible to enumerable pathologies including lip keratoses, chapping, dryness, fissuring, ulcerations, exudations, crusting, exfoliations, inflammation, infections, and edema.

No external portion of the human body is as active as the lips in terms of being closely associated with everyday human activities including oral communication, respiration and eating abilities. The location and structure of the lips result in those human activities being severely hampered, if any of the above abnormalities exist. As a consequence, when the lip must be treated as by the application of medication and/or protective covering or bandaging to the outer surface thereof using present methods it becomes very inconvenient to the patient, if not impractical per se. Further, there is a problem of maintaining the medication and/or protective covering on the effected area. Subconscious tongue probing, effects of saliva, and interaction with the opposing lip are examples of conditions that result in the wearing away of lip medication, preventing the uninterrupted natural healing process and causing constant irritation to the lip.

Heretofore there was no device that one could use to protect and prevent abnormalities from occurring to the lip and in addition be used by itself or in conjunction with medication for therapeutic purposes.

SUMMARY OF THE INVENTION

Accordingly, it is an object of this invention to provide a device that protects the lips from exposure. It is another object of this invention to provide a lip mounted device that can aid in the treatment of existing lip pathologies.

It is a further object of this invention to provide a lip mounted device that can be retained on the lip without adversely affecting normal breathing, speech, jaw movement and the like.

It is yet another object of this invention to provide a lip shade device, simplistic in its design and inexpensive in its construction.

According to the invention, there is provided a lip shade and treatment device that is easily retained on the lip. In the preferred embodiment of the invention, the lip shade and treatment device is an integral piece shaped to conform to the configuration of a normal lip. The U-shaped cross-section defines a first leg adapted to fit over the portion of the lip exterior of the mouth including the vermilion border and a second leg adapted to fit over the intra-oral surface of the lip when worn by the user. If desired, before mounting the device upon the lip, appropriate medication can be applied either directly on the lip or on the interior surface of the lip shade and treatment device so that when used with medication opposing lip contact, external irritation, undesired sequellae, lip biting, tongue investigation and other healing preventing action is avoided. In an alternative embodiment a lining of sponge-like material may be used on the interior surface of the device to more efficiently hold the medication. In still a further embodiment the device may be constructed of materials that are known to screen out or block various unwanted rays from the sun or other radiation emitting sources. In yet another embodiment the device can be made to have a hollow interior so that desired material can be inserted for blocking radiation or for other purposes.

In the preferred embodiment the "U"-shape cross-section is horseshoe shaped so that the legs of the "U" are closer together at the ends than at their middle so that the device is resiliently but securely maintained on the lip.

BRIEF DESCRIPTION OF THE DRAWINGS

FIG. 1 is a perspective view of the inventive lip shade and treatment device.

FIG. 2 is a cross-section taken along the lines of 2—2 in FIG. 1.

FIG. 3 is a diagrammatic side view of the inventive device mounted on the lower lip of a user.

FIG. 4 is a cross-section of and alternative embodiment of the lip shade and treatment device.

FIG. 5 is a cross-section of another alternative embodiment of the lip shade and treatment device.

DETAILED DESCRIPTION OF THE PREFERRED EMBODIMENT

Referring now to the drawings in detail, wherein like reference numerals indicate like parts throughout the several figures, reference numeral 20 represents the inventive lip shade and treatment device made of any suitable resilient material having the general outer configuration of a normal lip, and being flexible enough to fit various shaped lips.

Device 20 may be worn on either the upper or lower lip, but because the lower lip is known to be subjected to more frequent problems, all the below description will be directed to use of device 20 on the lower lip of the user.

When mounted upon the lip 30, as seen in cross-section in FIG. 4, the exterior leg 22 of device 20 covers the exterior vermilion surface of lip 30 and extends below the vermilion border 32 while leg 24 covers the intra-oral portion of lip 30 extending below the vermilion-mucosal border 34 which usually represents the highest point of dental contact of the inner lip. It is known that the maximum width of the cross-section of the lip can be generally represented by a line drawn from the vermilion border to the vermilion-mucosal border. In FIG. 4 the maximum width is represented by the dotted line connecting points 32 and 34. In the preferred embodiment of the lip shade and treatment device the shape of a cross-section of device 20 is seen in FIG. 2 to be a generally "U"-shaped horseshoe configuration in which the lower leg portions represented by points 24" and 22" converge to define a gradual decrease in the distance between the legs. The length of the legs of the "U" are sufficient so that the maximum width of device 20 will fit comfortably over the maximum width of lip 30 and the lower ends 22" and 24" of device 20 will comfortably serve to secure the device 20 on the lip 30. It can be appreciated that the shape of legs 22 and 24 may take various forms and as seen from the FIG. 4 cross-section of an alternative embodiment of the lip shade and treatment device represented by numeral 40, the legs of the "U" may be constructed so the lower ends thereof are substantially parallel. A further embodiment may include lower leg portions that diverge after converging so as to form a rounded support for the device.

Referring again to FIGS. 1-3, a lining 28 is shown to be located on the internal surface 26 of device 20 and is provided so that appropriate medication can be applied thereon when so desired. It can be appreciated in alternative embodiments that the lining 28 may be excluded from the device 20. Lining 20 may be made of any suitable material, but it has been found that a soft sponge-like material adhesively mounted is preferred. Lining 28 serves an additional function of providing a soft surface upon which the surface of the lip 30 may rest thus avoiding possible irritations should the lip 30 be tender from the existing pathologies located thereon or other reasons.

FIG. 5 is directed to an alternative embodiment wherein the lip shade and treatment device 50 has a hollow portion 52 within which any desired material may be introduced to screen or block various rays of the sun or other radiation emitting sources. It is understood that in any of the above described embodiments, materials having any desired physical characteristics including flexibility, weight, color, density, radiation absorption and the like may be used.

From the preceding description of the preferred embodiments, it is evident that the objects of the invention are obtained and a novel lip shield and treatment device is provided. Although the invention has been described in detail, it is clearly understood that the same is by way of illustration and example only and is not to be taken by way of limitation. The spirit and scope of this invention is to be limited by the terms of the appended claims.

We claim:

1. An improved lip shield adapted for comfortable and effective mounting on a single human lip, said human lip characterized as having an exterior vermilion surface ending at the vermilion border, an intra-oral surface ending at the vermilion-mucosal border, and a generally U-shaped horseshoe configured cross-section with said cross-section having a maximum width along an imaginary line connecting the point on said cross-section representing said vermilion border to the point on said cross-section representing said vermilion-mucosal border, said improved lip shield comprising a one-piece member having a first leg means for covering said exterior vermilion surface of said lip, a second leg means for covering said intra-oral surface of said lip, and further having a generally U-shaped horseshoe configured cross-section corresponding to said lip cross-section with the maximum distance between said first and second leg means being measured along an imaginary line connecting the point on said shield cross-section that covers said lip vermilion border to the point on said shield cross-section that covers said lip vermilion-mucosal border when said shield is mounted on said lip, said shield cross-section having first, second, and third portions, said first portion located on one side of said imaginary line representing the maximum distance between said first and second leg means and said second and third portions located on the other side of said imaginary maximum distance line and wherein the distance between any two points on respective first and second leg means located on said first portion of said shield cross-section is less than said maximum distance, and wherein the distance between any point on said first leg means located on said second portion and any point on said second leg means located on said third portion is less than said maximum distance.

2. The improved lip shield according to claim 1 wherein said first leg means extends over said lip vermilion border and said second leg means extends over said lip vermilion-mucosal border when mounted on said human lip.

3. The improved lip shield according to claims 1 or 2 wherein said first and second leg means are substantially parallel in said second and third portions of said shield cross-section and are connected in said first portion of said shield cross-section.

4. The improved lip shield according to claims 1 or 2 having a hollow chamber for holding material used to block various forms of radiation, said hollow chamber being completely surrounded by the walls of said lip shield.

5. The improved lip shield according to claims 1 or 2 having means located on the surface of said lip shield adapted to be in contact with said lip for maintaining medication to treat said lip thereon.

6. The improved lip shield according to claim 4 having means located on the surface of said lip shield adapted to be in contact with said lip for maintaining medication to treat said lip.

7. A lip shield device adapted for comfortable and effective mounting on a human lip comprising a member having the general outer configuration of the shape of a normal lip and a generally U-shaped configured cross-section wherein said device has a hollow chamber for holding material used to block various forms of radiation said hollow chamber being completely surrounded by the walls of said lip shield.

8. A lip shield device according to claim 7 having a first leg means for extending over the vermilion border of said lip and second leg means for extending over the vermilion-mucosal border of said lip when said shield device is mounted on said lip.

9. A lip shield device according to claim 8 wherein said first and second leg means are substantially parallel.

10. A lip shield device according to claims 7, 8 or 9 having means located on the surface thereof adapted to be in contact with said lip for maintaining medication to treat said lip.

* * * * *